United States Patent [19]
Engler et al.

[11] Patent Number: 6,165,779
[45] Date of Patent: Dec. 26, 2000

[54] COMPOSITIONS AND METHODS FOR THERAPEUTIC USE

[75] Inventors: Heidrun Engler; Bernard G. Huyghe; Daniel C. Maneval; Paul Shabram, all of San Diego, Calif.

[73] Assignee: Canji, Inc., San Diego, Calif.

[21] Appl. No.: 08/779,627

[22] Filed: Jan. 7, 1997

Related U.S. Application Data

[63] Continuation-in-part of application No. 08/584,077, Jan. 8, 1996, Pat. No. 5,789,244.

[51] Int. Cl.$^7$ .............................. C12N 15/63; C12N 7/00; A61K 38/00; A61K 48/00
[52] U.S. Cl. .................. 435/320.1; 435/235; 424/199.1; 514/44
[58] Field of Search ................................ 514/44; 935/52, 935/54; 536/23.1, 23.5; 435/320.1, 172.3, 450

[56] References Cited

U.S. PATENT DOCUMENTS 5,552,309  9/1996  March .
5,912,236  6/1999  Xu et al. .................................... 514/44

FOREIGN PATENT DOCUMENTS

95/11984   5/1995   WIPO ............................ C12N 15/86

OTHER PUBLICATIONS

Wills et al. Sep. (1994) Human Gene Ther., vol. 5, 1079–1088.
Hjelmeland et al. (1983) Anal. Biochem., vol. 130, 485–490.
Pinnaduwage et al. (1989) Biochim. Biophys. Acta., vol. 985, 33–37.
Osifchin et al. Mar. (1994) J. Biol. Chem., vol. 269 (9), 6383–6389.
Takahashi et al. Jun. (1991) Proc. Natl. Acad. Sci. USA., vol. 88, 5257–5261.
Miller et al Feb. (1995) FASEB J. 9:190–199.
Marshall, E Aug. 25, (1995) Science 269:1050–1055.
Greney et al (1994) Neurochem. Int. 25:183–191.
Pinnaduwage et al (1989) Biochemica et Biophysica Acta 985:33–37.
Abe, A. et al., "Transduction of a Drug–Sensitive Toxic Gene into Human Leukemia Cell Lines with a Novel Retroviral Vector (43611) ,"*Proc. Soc. Exp. Biol. Med.* 203:354–359 (1993).
Banjerjee, A. et al., "Changes in Growth and Tumorigenicity Following Reconstitutionof Retinoblastoma Gene Function in Various Human Cancer Cell types by Microcell Transfer of Chromosome 13," *Canc. Res.* 52:6297–6304 (1992).
Bass, C. et al., "Recombinant Adenovirus–Mediated Gene Transfer to Genitourinary Epithelium in Vitro and In Vivo," *Canc. Gene Ther.* 2(2) :97–104 (1995).
Blixt et al., "Enhancement of Intracellular Uncoating of Adenovirus in HeLa cells in the Presence of Benzyl Alcohol as a Membrane Fluidizer," *Arch. Virol.* 129:265–277 (1993).
Brewster et al., *Eur. Urol.* 25:177–182 (1994).
Cairns et al., "Loss of heterozygosity at the RB Locus is Frequent and Correlates with Muscle Invasion in Bladder Carcinoma," *Oncogene* 6:2305–2309 (1991).
Cancer Facts and Figures, *Amer. Can. Soc.* 5–11 (1995).
Fujimoto, K. et al., "Frequent Association of p53 Gene Mutation in invasive Bladder Cancer, " *Canc. Res.* 52:1393–1398 (1992).
Ginsberg, H.S. et al., "Role of early region 3 (E3) in pathogenesis of adenovirus disease," *Proc. Natl. Acad. Sci. U.S.A.* 86:3823–3827 (1989).
Good et al., *Biochemistry* 5:467 (1966).
Goodrich, D.W. et al., "Expression of the Retinoblastoma Gene Product in Bladder Carcinoma Cell Associates with a Low Frequency of Tumor Formation," *Canc. Res.* 52:1968–1973 (1992).
Greenberg, R. et al., "Intravesical AD 32 (N–Trifluoroacetyladriamycin–14–Valerate) in the Treatment of Patients with Refractory Bladder Carcinoma–Clinical Efficacy, Pharmacology, and Safety," *Proc. Amer. Urol. Assoc.* 153 Supp 233A:19 (1995).
Hemstrom, C. et al., "Gene Product of Region E4 of Adenovirus Type 5 Modulates Accumulation of Certain Viral Polypeptides," *J. Virol.* 62(9) :3258–3265 (1988).
Li, Q. et al., "Assessment of Recombinant Adenoviral Vectors for Hepatic Gene Therapy," *Human Gene Ther.* 4:403–409 (1993).
Monson, F.C. et al., "Indigocarmine as a Quantitative Indicator of Urothelial Integrity," *J. Urol.* 145:842–845 (1991).
Morris, B.D. et al., "Adenoviral–Mediated Gene Transfer to Bladder In Vivo," *J. Urol.* 152:506–509 (1994).
Parsons, C.L. et al., "Bladder Surface Gycosaminoglycans: An Epithelial Permeability Barrier," *J. Urol.* 143:139–142 (1990).
Rosenberg, S.A., "The Immunotherapy and Gene Therapy of Cancer," *J. Clin. Oncol.* 10 (2) : 180–199 (1992).
Sandberg, J.W. et al., "Improving Access to Intestinal Stem Cells as a Step Toward Intestinal Gene Transfer," *Hum. Gene Ther.* 5:323–329 (1994).
Spandidos, D.A. et al., "Expression of the Normal H–ras1 Gene Can Suppress the Transformed and Tumorigenic Phenotypes Induced by mutant ras Genes," *Anticancer Res.* 10:1543–1554 (1990).
Takahashi, R. et al., "The Retinoblastoma Gene Functions as a Growth and Tumor Suppressor in Human Bladder Carcinoma Cells," *Proc. Natl. Acad. Sci. U.S.A.* 88:5257–5261 (1991).
Wills, K.N. et al., "Development and Characterization of Recombinant Adenoviruses Encoding Human p53 for Gene Therapy of Cancer," *Human Gene Ther.* 5:1079–1088 (1994).
Wills, K.N. et al., "Gene therapy for hepatocellular carcinoma: Chemosensitivity conferred by adenovirus–mediated transfer of the HSV–1 thymidine kinase gene," *Canc. Gene Ther.* 2(3) :191–197 (1995).

*Primary Examiner*—Karen M. Hauda
*Assistant Examiner*—Anne Marie S. Beckerleg
*Attorney, Agent, or Firm*—Townsend and Townsend and Crew LLP

[57] ABSTRACT

A method and pharmaceutical composition for the treatment of cancer using a gene delivery system, such as a viral vector delivery system, comprising a therapeutic gene such as p53 or a retinoblastoma tumor suppressor gene wherein the gene delivery system is formulated in a buffer comprising a delivery-enhancing agent such as ethanol or a detergent.

9 Claims, 13 Drawing Sheets

COMPOSITIONS AND METHODS FOR THERAPEUTIC USE

This application is a continuation-in-part of U.S. Ser. No. 08/584,077, filed Jan. 8, 1996 which issued as U.S. Pat. No. 5,789,244 on Aug. 4, 1998.

BACKGROUND OF THE INVENTION

The present invention is directed to compositions and methods of treating cancer by gene therapy using a therapeutic gene, such as a tumor suppressor gene delivered by a gene delivery system, such as a recombinant viral vector delivery system, formulated in a buffer comprising a delivery-enhancing agent. In particular, this invention relates to the delivery of a tumor suppressor gene (e.g., p53 or retinoblastoma (RB)) to cancerous epithelial tissues and organs, such as the bladder, using a recombinant adenoviral vector delivery system formulated in a buffer comprising a delivery-enhancing agent.

Carcinoma of the bladder represents a significant source of morbidity and mortality. Bladder cancer ranks 10th in males and 12th in females in cancer related mortality (Cancer Facts and Figures, *Amer.Can.Soc.* 5:11 (1995)). Therapies available for the treatment of bladder cancer include adjuvant chemotherapy or immunotherapy, transurethral resection of superficial disease, radical cystectomy or radiotherapy which is often combined with systemic chemotherapy. Despite these therapeutic options, overall survival has not changed appreciably. (Ibid) Thus, new therapeutic modalities must be developed for the treatment of bladder cancer.

Gene therapy strategies have been developed as an alternative therapeutic approach (See for example, Brewster et al. *Eur Urol* 25:177–182 (1994); Takahashi et al., *Proc Natl Acad Sci USA* 88: 5257–5261 (1991); Rosenberg, S A, *J. Clin Oncol.* 10:180–199 (1992)).

Distinct approaches have been developed to treat neoplasms based on gene transfer methods. Methods have been developed to correct specific lesions at defined genetic loci which give rise to neoplastic transformation and progression (Spandidos et al., *Anticancer Res.* 10:1543–1554 (1990); Banerjee et al. *Cancer Res.* 52:6297–6304 (1992)). Overexpression of dominant oncogenes may be addressed using techniques to inhibit the transforming gene or gene product. Loss of tumor suppressor gene function may be approached using methods to reconstitute wild-type tumor suppressor gene function (Goodrich et al., *Cancer Res.* 52:1968–1973 (1992)). Besides these methods to achieve mutation compensation, genetic techniques have been developed to specifically and selectively eradicate tumor cells. These approaches of molecular chemotherapy rely on specific expression of toxin genes in neoplastic cells (Abe et al., *Proc Soc Exp Biol Med.* 203:354–359 (1993)). Finally, gene transfer methods have been used to achieve antitumor immunization. These methods of genetic immunopotentiation use techniques of genetic immunoregulation to enhance immune recognition of tumors. Consequently, a variety of distinct approaches have been developed to accomplish gene therapy of cancer.

A high incidence of mutations has been observed in tumor suppressor genes, such as p53 and RB, in the case of carcinoma of the bladder (Fujimoto et al. *Cancer Res.* 52:1393–1398 (1992); Cairns et al. *Oncogene* 6:2305–2309 (1991)). For such genetic lesions of tumor suppressor genes, reversion of the neoplastic phenotype can be demonstrated with replacement of the corresponding wild-type tumor suppressor gene (Spandidos, Id.; Banerjee, Id.).

In vitro studies using cell lines derived from human bladder tissues have demonstrated efficient transgene expression following infection with recombinant adenovirus (Bass et al. *Cancer Gene Therapy* 2:2:97–104 (1995)). Experiments in vivo have also shown adenovirus transgene expression in the urinary bladder of rodents after intravesical administration (Ibid; Morris et al. *J. Urology.* 152:506–50 (1994)). In vitro experiments with wild-type adenovirus demonstrate that virus attachment and internalization is not influenced by benzyl alcohol, but do demonstrate an enhanced uncoating of the virion (Blixt et al. *Arch. Virol.* 129:265–277 (1993)). In vivo efforts with agents (e.g. acetone, DMSO, prolamine sulfate) can break down the protective "mucin" layer that protects the bladder epithelium from bacteria, viruses and other pathogens (Monson et al. *J. Urol.* 145:842–845 (1992); Parsons et al. *J. Urol.* 143:139–142 (1990)). None of the methods tried to date achieve enhanced delivery of a therapeutic tumor suppressor gene to the bladder for the treatment of bladder cancer. In order to accomplish gene therapy for treatment of bladder cancer, gene therapy methods must be developed to accomplish direct, optimal, in vivo tumor suppressor gene delivery to the bladder epithelium.

These needs and others are addressed by the instant invention.

SUMMARY OF THE INVENTION

One aspect of the invention is a method of administering a therapeutic agent to a tissue having an epithelial membrane, comprising administering a therapeutically effective amount of the therapeutic agent formulated in a buffer comprising a detergent.

A further aspect of the invention is a pharmaceutical composition comprising a therapeutically effective amount of the therapeutic agent formulated in a buffer comprising a detergent.

A further aspect of the invention is a method of treating bladder cancer comprising administration of a therapeutically effective amount of a therapeutic gene contained within a gene delivery system that is formulated in a buffer comprising a delivery-enhancing agent.

A further aspect of the invention is a pharmaceutical formulation for administration of a recombinant adenovirus, comprising about $10^9$–$10^{11}$ particles (PN)/ml recombinant adenovirus, about 2–10 mM Big CHAP or about 0.1–1.0 mM TRITON®-X-100 detergent, phosphate buffered saline (PBS), about 2–3% sucrose (w/v) and about 1–3 mM $MgCl_2$, about pH 6.4–8.4.

DETAILED DESCRIPTION OF THE INVENTION

Figure 1:
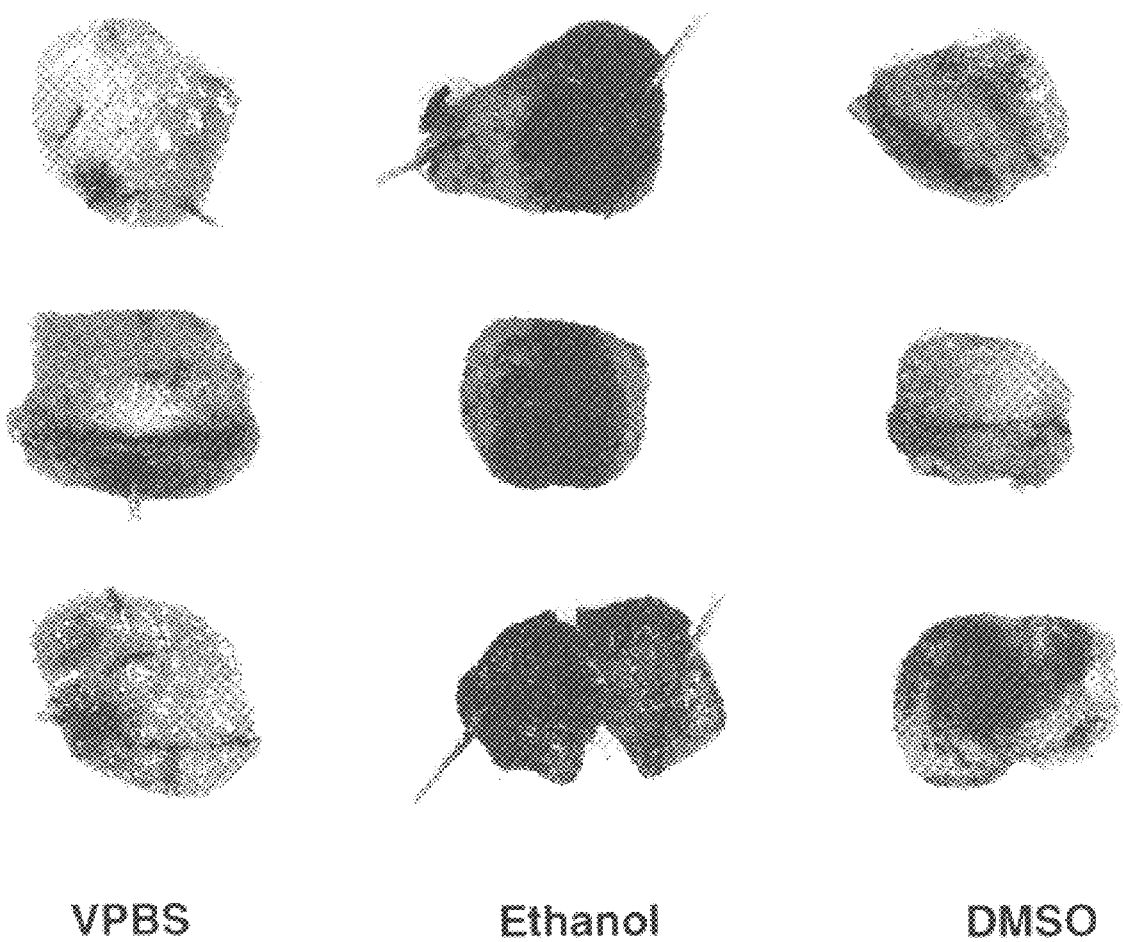
FIG. 1 depicts the influence of formulation on adenovirus mediated gene transfer and expression in the rat bladder epithelium after intravesical administration.

As used herein, "a gene delivery system" refers to any means of delivery of a therapeutic gene to a particular epithelial tissue or organ including, for example, recombinant vectors and non-vector systems. Examples of non-vector systems include but are not limited to any lipid-based, lipid encapsulated DNA or cationic lipid/DNA complexes. Examples of recombinant viral vectors include but are not limited to herpes virus, retrovirus, vaccinia virus, adenovirus, and adenoassociated virus. "Recombinant" refers to nucleic acids and protein encoded by them wherein the nucleic acids are constructed by methods of recombinant DNA technology, also termed "genetic engineering". A preferred recombinant viral vector is the adenoviral vector delivery system which has a deletion of the protein IX gene (See International Patent Application WO 95/11984, which is herein incorporated by reference in its entirety for all purposes). The recombinant vector delivery system comprising a therapeutic gene, such as a tumor suppressor gene, is formulated in a buffer comprising a delivery enhancing agent. "A delivery-enhancing agent" refers to any agent which enhances delivery of a therapeutic gene, such as a tumor suppressor gene to a cancerous tissue or organ. Such enhanced delivery may be achieved by various mechanisms. One such mechanism may involve the disruption of the protective glycosaminoglycan layer on the epithelial surface of the bladder. Examples of such delivery-enhancing agents are detergents, alcohols, glycols, surfactants, bile salts, heparin antagonists, cyclooxygenase inhibitors, hypertonic salt solutions, and acetates. Alcohols include for example the aliphatic alcohols such as ethanol, N-propanol, isopropanol, butyl alcohol, acetyl alcohol. Glycols include glycerine, propyleneglycol, polyethyleneglycol and other low molecular weight glycols such as glycerol and thioglycerol. Acetates such as acetic acid, gluconol acetate, and sodium acetate are further examples of delivery-enhancing agents. Hypertonic salt solutions like 1M NaCl are also examples of delivery-enhancing agents. Examples of surfactants are sodium dodecyl sulfate (SDS) and lysolecithin, polysorbate 80, nonylphenoxypolyoxyethylene, lysophosphatidylcholine, polyethylenglycol 400, polysorbate 80, polyoxyethylene ethers, polyglycol ether surfactants and DMSO. Bile salts such as taurocholate, sodium tauro-deoxycholate, deoxycholate, chenodesoxycholate, glycocholic acid, glycochenodeoxycholic acid and other astringents like silver nitrate may be used. Heparin-antagonists like quaternary amines such as prolamine sulfate may also be used. Cyclooxygenase inhibitors such as sodium salicylate, salicylic acid, and non-steroidal antiinflammatory drug (NSAIDS) like indomethacin, naproxen, diclofenac may be used.

Detergents include anionic, cationic, zwitterionic, and nonionic detergents. Exemplary detergents include but are not limited to taurocholate, deoxycholate, taurodeoxycholate, cetylpyridium, benalkonium chloride, ZWITTERGENT®3-14 detergent, CHAPS (3-[(3-Cholamidopropyl)dimethylammoniol]-1-propanesulfonate hydrate, Aldrich), Big CHAP, Deoxy Big CHAP, TRITON®-X-100 detergent, C12E8, Octyl-B-D-Glucopyranoside, PLURONIC®-F68 detergent, TWEEN® 20 detergent, and TWEEN® 80 detergent (CALBIOCHEM® Biochemicals).

In an embodiment, the delivery-enhancing agent is included in the buffer in which the recombinant adenoviral vector delivery system is formulated. The delivery-enhancing agent may be administered prior to the recombinant virus or concomitant with the virus. In some embodiments, the delivery-enhancing agent is provided with the virus by mixing a virus preparation with a delivery-enhancing agent formulation just prior to administration to the patient. In other embodiments, the delivery-enhancing agent and virus are provided in a single vial to the caregiver for administration.

In the case of a pharmaceutical composition comprising a tumor suppressor gene contained in a recombinant adenoviral vector delivery system formulated in a buffer which further comprises a delivery-enhancing agent, the pharmaceutical composition may be administered over time in the range of about 5 minutes to 3 hours, preferably about 10 minutes to 120 minutes, and most preferably about 15 minutes to 90 minutes. In another embodiment the delivery-enhancing agent may be administered prior to administration of the recombinant adenoviral vector delivery system containing the tumor suppressor gene. The prior administration of the delivery-enhancing agent may be in the range of about 30 seconds to 1 hour, preferably about 1 minute to 10 minutes, and most preferably about 1 minute to 5 minutes prior to administration of the adenoviral vector delivery system containing the tumor suppressor gene.

The concentration of the delivery-enhancing agent will depend on a number of factors known to one of ordinary skill in the art such as the particular delivery-enhancing agent being used, the buffer, pH, target tissue or organ and mode of administration. The concentration of the delivery-enhancing agent will be in the range of 1% to 50% (v/v), preferably 10% to 40% (v/v) and most preferably 15% to 30% (v/v). Preferably, the detergent concentration in the final formulation administered to the patient is about 0.5–2× the critical micellization concentration (CMC). A preferred concentration of Big CHAP is about 2–20 mM, more preferable about 3.5–7 mM.

The buffer containing the delivery-enhancing agent may be any pharmaceutical buffer such as phosphate buffered saline or sodium phosphate/sodium sulfate, Tris buffer, glycine buffer, sterile water and other buffers known to the ordinarily skilled artisan such as those described by Good et al. (1966) *Biochemistry* 5:467. The pH of the buffer in the pharmaceutical composition comprising the tumor suppressor gene contained in the adenoviral vector delivery system, may be in the range of 6.4 to 8.4, preferably 7 to 7.5, and most preferably 7.2 to 7.4.

A preferred formulation for administration of a recombinant adenovirus is about $10^9$–$10^{11}$ PN/ml virus, about 2–10 mM Big CHAP or about 0.1–1.0 mM TRITON®-X-100 detergent, in phosphate buffered saline (PBS), plus about 2–3% sucrose (w/v) and about 1–3 mM $MgCl_2$, at about pH 6.4–8.4.

The term "enhanced" describes the increased delivery of the therapeutic gene, such as a tumor suppressor gene, to the cancerous tissue or organ. Increased delivery of a therapeutic gene, such as a tumor suppressor gene, can be measured by various means, for example by measuring expression of the tumor suppressor gene compared to expression levels when the tumor suppressor gene is delivery in an adenoviral vector delivery system in a buffer lacking the delivery-enhancing agent. Examples of therapeutic genes are tumor suppressor genes and the suicide gene thymidine kinase. Examples of tumor suppressor genes include but are not limited to p53, the retinoblastoma gene, either full length ($p110^{RB}$) or fragments thereof such as $p94^{RB}$ or $p56^{RB}$, and p16. Other therapeutic genes include but are not limited to CFTR, genes encoding cytokines (such as the interferons α, β, γ, δ, interleukins (e.g., IL-4, IL-10, IL-2), GM-CSF, and any other genes encoding proteins which have therapeutic potential in the treatment of non-cancerous diseases of the bladder such as cystitis. In some embodiments of the invention, the therapeutic gene encodes antisense RNA.

In some embodiments, the compositions of the invention comprise a therapeutically effective amount of a therapeutic gene, such as a tumor suppressor gene contained in a recombinant viral vector delivery system in a buffer comprising a delivery-enhancing agent. "Therapeutically effective" as used herein refers to the prevention of, reduction of, or curing of symptoms associated with a disease state.

Therapeutically effective amounts of the pharmaceutical composition comprising a therapeutic gene, such as p53 or the retinoblastoma tumor suppressor gene, in a recombinant viral vector delivery system formulated in a buffer comprising a delivery-enhancing agent will be administered in accord with the teaching of this invention. For example, therapeutically effective amounts of the retinoblastoma tumor suppressor gene in the recombinant adenoviral vector delivery system formulated in a buffer containing a delivery-enhancing agent are in the range of about $1\times10^8$ particles/ml to $1\times10^{12}$ particles/ml, more typically about $1\times10^8$ particles/ml to $5\times10^{11}$ particles/ml, most typically $1\times10^9$ particles/ml to $1\times10^{11}$ particles/ml (PN/ml).

The compositions of this invention may additionally include a stabilizer, enhancer or other pharmaceutically acceptable carriers or vehicles. A pharmaceutically acceptable carrier can contain a physiologically acceptable compound that acts, for example, to stabilize the recombinant adenoviral vector delivery system comprising the tumor suppressor gene. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. One skilled in the art would know that the choice of pharmaceutically acceptable carrier, depends on the route of administration and the particular physio-chemical characteristics of the recombinant adenoviral vector delivery system and the particular tumor suppressor gene contained therein.

Examples of carriers, stabilizers or adjuvants can be found in Martin, *Remington's Pharm.Sci.*, 15th Ed. (Mack Publ. Co., Easton, Pa. 1975), incorporated herein by reference.

The recombinant viral vector delivery system comprising a therapeutic gene formulated in a buffer comprising a delivery-enhancing agent may be delivered to any cancerous tissue or organ using any delivery method known to the ordinarily skilled artisan for example, intratumoral or intravesical administration. Cancerous tissues and organs include any tissue or organ having an epithelial membrane such as the gastrointestinal tract, the bladder, respiratory tract, and the lung. Examples include but are not limited to carcinoma of the bladder and upper respiratory tract, vulva, cervix, vagina or bronchi; local metastatic tumors of the peritoneum; broncho-alveolar carcinoma; pleural metastatic carcinoma; carcinoma of the mouth and tonsils; carcinoma of the nasopharynx, nose, larynx, oesophagus, stomach, colon and rectum, gallbladder, or skin; or melanoma.

The delivery-enhancing agents of the invention can also be used to formulate other pharmaceutical agents, such as proteins, nucleic acids, antisense RNA, small molecules, etc., for administration to any tissue or organ having an epithelial membrane.

The following examples are intended to illustrate, not limit the scope of this invention.

EXPERIMENTAL EXAMPLES

Example 1

Ethanol Improves Gene Transfer in the Bladder

Initial experiments have shown that several factors including virus concentration, time of administration, and volume of dosing can influence gene transfer to the bladder epithelium after intravesical administration to rats. Because increased penetration of dyes can be achieved by intravesical administration of different solvents, modification of the adenovirus formulation was also investigated as an alternative strategy to increase adenovirus transgene expression in the bladder (Monson et al. *Urology* 145:842–845 (1991)). The instant experiments focused on the use of ethanol to increase adenovirus transgene expression in the bladder.

Nine female buffalo rats (Harlan Sprague Dawley) were anesthetized with isoflurane and received a single intravesical administration of a human recombinant adenovirus encoding the lacZ gene (rAd-βgal). The human recombinant adenoviral vector comprising the lacZ gene (rAd-βgal) is described in Wills et al. *Human Gene Therapy* 5:1079–1088 (1994). Before instillation bladders were flushed with PBS and emptied. rAd-βgal was then diluted to achieve a final concentration of $1.7\times10^{11}$ PN/mL in 1) VPBS (2% (w/v) sucrose and 2 mM MgCl, in PBS), 2) 30% (v/v) ethanol, or 3) 50% (v/v) DMSO, and instilled in a 250 μL volume (N=3 animals/group). The administered material was retained in the bladder for 45 minutes. The bladder were then flushed with PBS, and the animals were permitted to recover from the procedure. Two days after administration, rats were sacrificed, bladders were harvested, fixed, and whole organs were stained with an Xgal (5-Bromo-4-chloro-3-indolyl-β-D-galactoside) solution to evaluate reporter gene transfer. Xgal-stained tissues were then paraffin embedded, sectioned, and counter stained with hematoxylin and eosin. Hydrolysis of Xgal by β-galactosidase results in a blue color that localized to the superficial luminal bladder epithelium.

Figure 2:
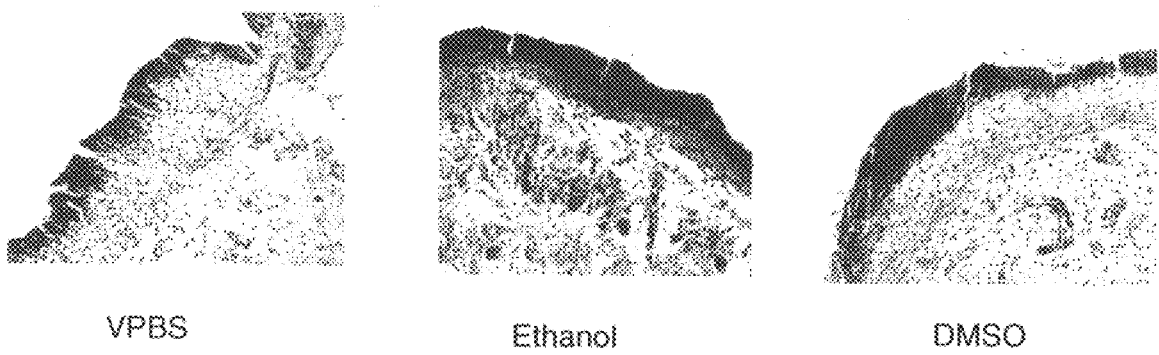
FIG. 2 depicts adenovirus transgene expression in bladder epithelial cells after intravesical administration.

Transgene expression, consequent to delivery by the adenoviral vector, was detected in bladders from all animals treated with rAd-βgal but not in an untreated control. Transgene expression was similar to previously published results using the PBS/sucrose formulation (Bass et al. *Cancer Gene Therapy* 2:2:97–104 (1995)). In sharp contrast, β-galactosidase expression in the luminal epithelial surface was greatly enhanced in animals that received rAd-βgal diluted in 30% ethanol (FIG. 1). Bladder specimens described in FIG. 1 were embedded, sectioned, and counter stained with hematoxylin and eosin. Histologic evaluation of the bladder tissue demonstrated increased β-galactosidase expression of the transitional bladder epithelium when ethanol was added to the adenovirus formulation (FIG. 2). The interaction of ethanol with the protective glycosaminoglycan (GAG) layer on the epithelium surface provides a mechanism for the observed increase in transgene expression. Disruption of this layer may facilitate virus-cell interaction at the surface and potentially enhance penetration into the submucosa.

Example 2

Dose-Dependent Transgene Expression in the Rat Bladder

Figure 3:
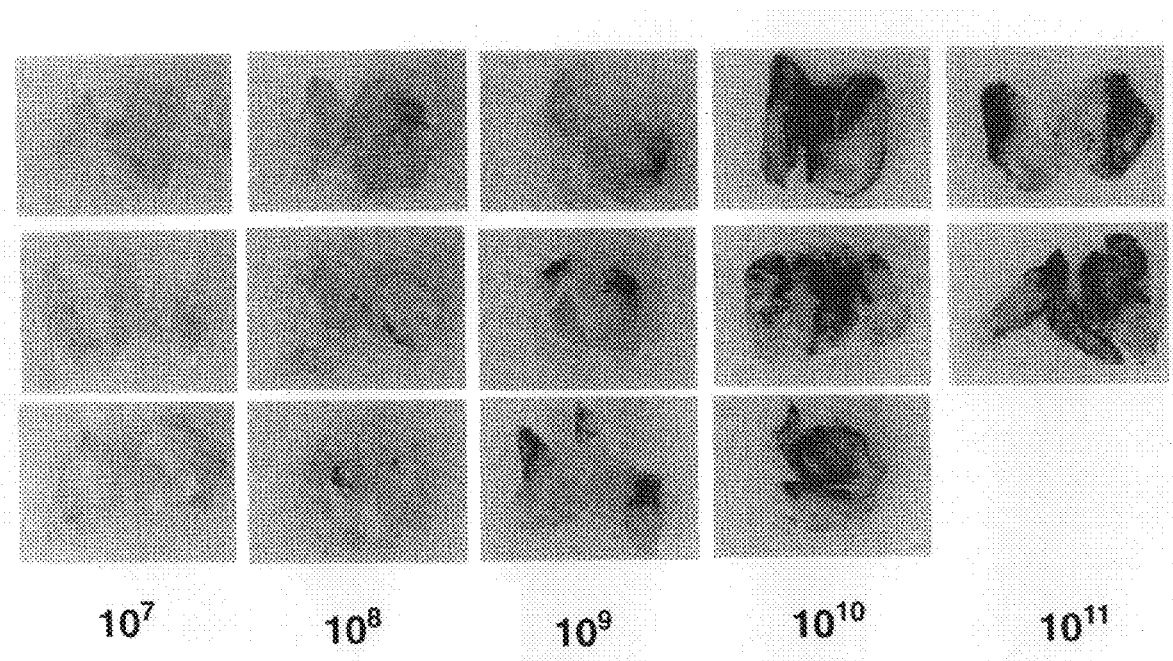
FIG. 3 depicts dose dependent adenovirus transgene expression in the rat bladder after intravesical administration.

In another experiment, 18 female Sprague-Dawley rats were anaesthetized with isoflurane and received a single 0.5 ml intravesical bolus of rAd-βgal at concentrations of $2\times10^7$, $2\times10^8$, $2\times10^9$, $2\times10^{10}$, and $2\times10^{11}$, PN/mL in a 22.5% (v/v) ethanol formulation. After a 45 minute incubation, the bladders were flushed with PBS, and animals were permitted to recover from anesthesia. Two days later, animals were sacrificed, and bladders were harvested, fixed, and whole organs were stained with Xgal solution to evaluate adenovirus transgene expression. β-galactosidase expression in the luminal bladder epithelium correlated with the concentration of the administered recombinant adenovirus (FIG. 3). No striking differences were observed among animals receiving $2\times10^{10}$ or $2\times10^{11}$ PN/mL, suggesting a saturation of transgene expression in this model: Analysis of the volume voided after instillation indicated only a minimal reduction in the infectious titer of the dosing material at these high doses. Expression of β-galactosidase decreased at lower concentrations. No evidence of β-galactosidase expression was detected in animals dosed at a concentration of $1\times10^7$ PN/mL or in an untreated control animal.

Example 3

ACNRB Gene Transfer in the Mouse Bladder

A pilot study was conducted to specifically evaluate expression of the RB transgene using a RT-PCR assay. The recombinant adenovirus used in this study was based on serotype 5 human adenovirus from which the viral early region 1 encoding E1a, E1b, and pIX proteins have been deleted. This adenovirus is limited to propagation in 293 cells which produce the Ad5 E1 gene products required for replication. Transfer plasmids encoding either full length or truncated Rb were generated from pACN (Wills et al. *Cancer Gene Therapy* 2:191–197 (1995)) and were, in turn, used to construct the recombinant adenoviruses. Either a full-length RB cDNA (1–928 amino acids), subcloned as a 2.8 Kb Xba I—Bam HI fragment from the plasmids pETRbc (Huang et al. *Nature* 350:160–162 (1991) or a truncated fragment (amino acids 381–928), subcloned as a 1.7 KB Xba I—Bam HI cDNA fragment, was placed downstream of the CMV promoter/enhancer and the Ad 2 tripartite leader cDNA of the plasmid pACN. These plasmids were subsequently linearized with Eco RI and cotransfected ($CaPO_4$, Stratagene) with either the isolated Cla I digested large fragment of H5ilE4 (Hemstrom et al. *J. Virol.* 62:3258–3264 (1988)), to make Ad-RB56 (ACN56) containing a partial E4 deletion, or with the large fragment from a hybrid virus of dl327 (Ginsberg et al. *Proc. Natl. Acad. Sci. U.S.A.* 86:3823–3827 (1989)) and H5ilE4 to create Ad-Rb110 (ACNRB) which contains deletions in both the E3 and E4 regions of the vector.

Figure 4:
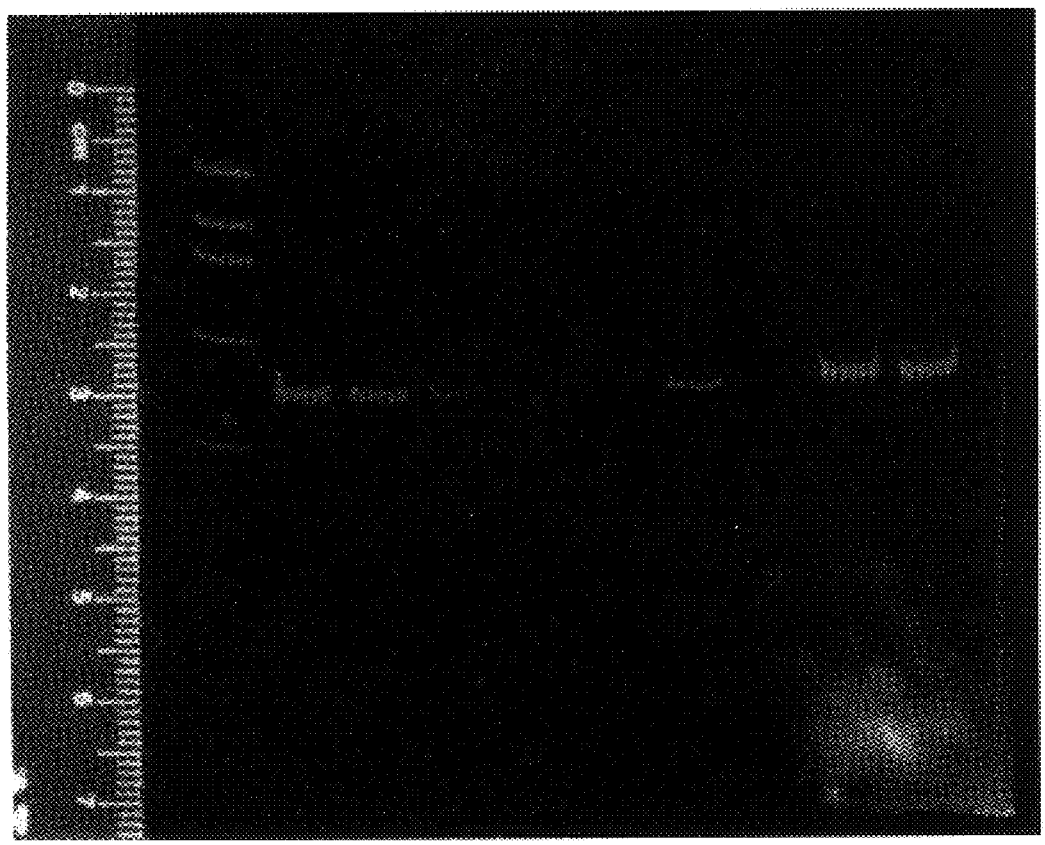
FIG. 4 depicts a reverse-transcriptase polymerase chain reaction (RT-PCR) analysis of recombinant adenovirus transgene expression in the mouse bladder after intravesical administration.

Eight female ICR mice (Charles River Laboratories) were anesthetized with avertine and each received a single 80 μl intravesical administration of (ACNRB). ACNRB ($4\times10^{11}$ PN/mL) was diluted and prepared in a PBS solution or a 30% (v/v) ethanol solution. After the virus was retained in the bladder for 45 minutes, the animals were permitted to recover and void. Mice were sacrificed 2 days or 14 days after ACNRB administration, and bladders, livers, and kidneys from each animal were harvested, homogenized, and processed for analysis (N=2 animals/group). Transgene expression was determined using RT-PCR with a primer specific for ACNRB. More specifically, primers were generated to identify ACNRB and amplify the region from the 3' end of the CMV sequence and to the 5' end of the RB sequence. Following amplification (30 cycles) RT-PCR products were separated on a 10% polyacrylamide gel, stained with ethidium bromide, and photographed. Increased ACNRB expression was detected after treatment with ACNRB in 30% (v/v) ethanol compared to very low expression after treatment with ACNRB in VPBS. Positive controls for the assay included samples from ACNRB-infected 5637 human bladder cancer cells (CONTROL). Bladder RNA samples from ACNRB-infected animals that were amplified with primers specific for beta-actin provided an internal control for the quality of RNA. Untreated samples and bladder samples without the reverse transcriptase (RT) provided controls for contaminating DNA. Two days after dosing, levels of ACNRB expression in the bladder homogenates were detected from animals that received ACNRB prepared in 30% ethanol (FIG. 4). No evidence of expression was detected in non-bladder tissue or in any samples collected 14 days after dosing.

Example 4

Kinetics of Biodistribution and ACNRB Expression After Intravesical Administration to Mice To investigate the time course of expression after intravesical administration, 40 female mice (Charles River Laboratories) were anaesthetized with avertine and received a single 80 μL bolus of ACNRB ($4\times10^{10}$ PN/mL in 22% (v/v) ethanol). The instilled material was retained in the bladder for approximately 45 minutes, and animals were permitted to recover from the procedure. Mice were sacrificed 1, 2, 3, 4, 5, 6, 7, and 14 days after administration (N=4/time) for analysis. Bladders, livers, and kidneys were harvested and snap frozen in liquid nitrogen for subsequent analysis. For detection of ACNRB expression, tissue samples were homogenized, and total RNA was extracted using TRI-Reagent®. An aliquot of total RNA was amplified in an RT-PCR assay using primers specific for ACNRB to distinguish transgene expression from endogenous RB expression. For detection of ACNRB DNA, a DNA extraction kit (Stratagene) was used on tissue homogenates. PCR was performed with the primers specific for ACNRB, as described above for the RT-PCR analysis.

Figure 5:
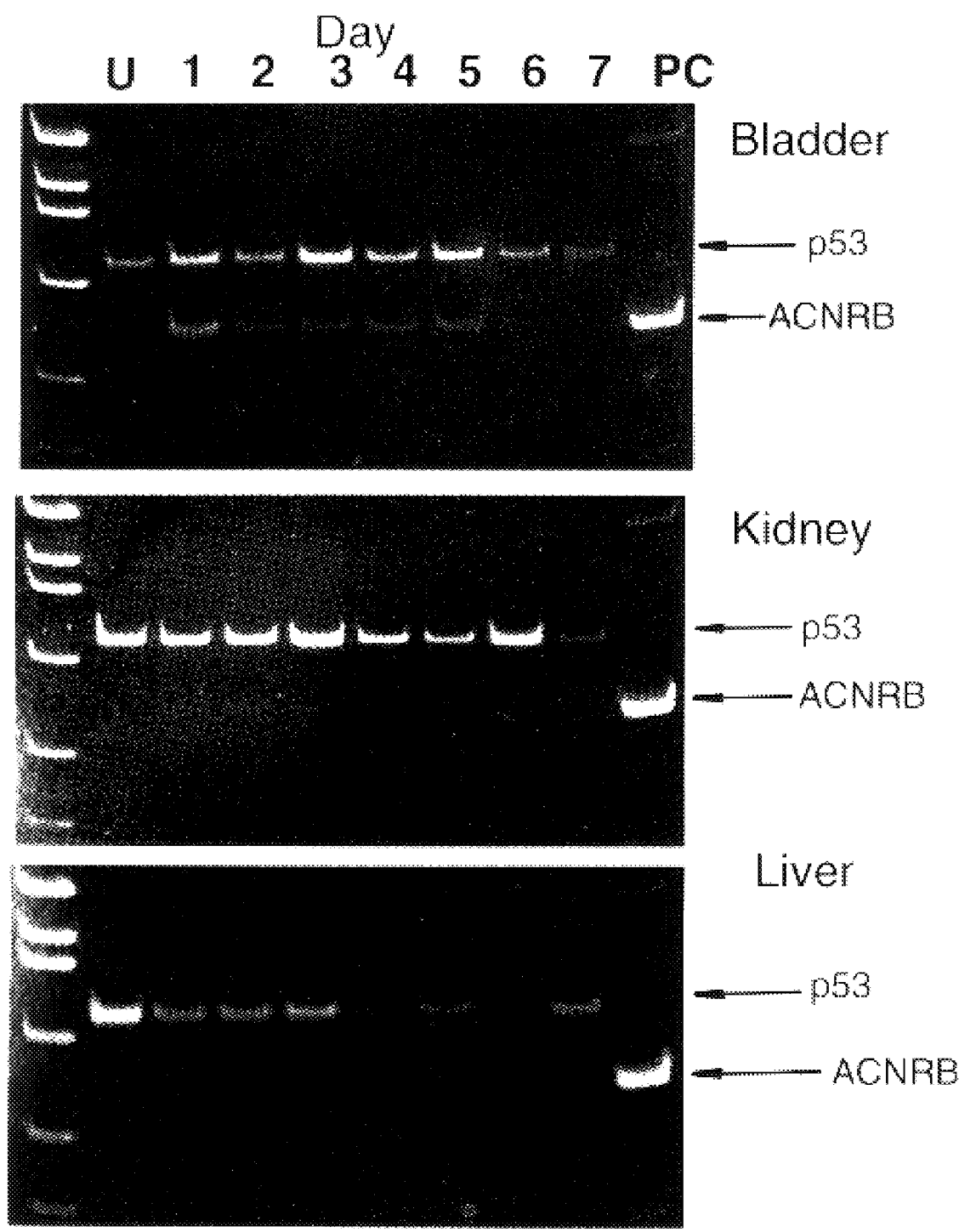
FIG. 5 depicts a time course of recombinant adenovirus transgene expression in bladder, kidney, and liver tissue after intravesical administration of the virus.

ACNRB transgene expression in the bladder homogenates was detected only in samples collected on days 1–6, with expression relative to endogenous p53 decreasing with time (FIG. 5, upper panel). No expression was detected from samples collected 7 and 14 days after administration. Interestingly, some ACNRB expression was detected in the kidneys on days 1, 2 and 3, but no expression was observed in the liver (FIG. 5, lower panels).

Figure 6:
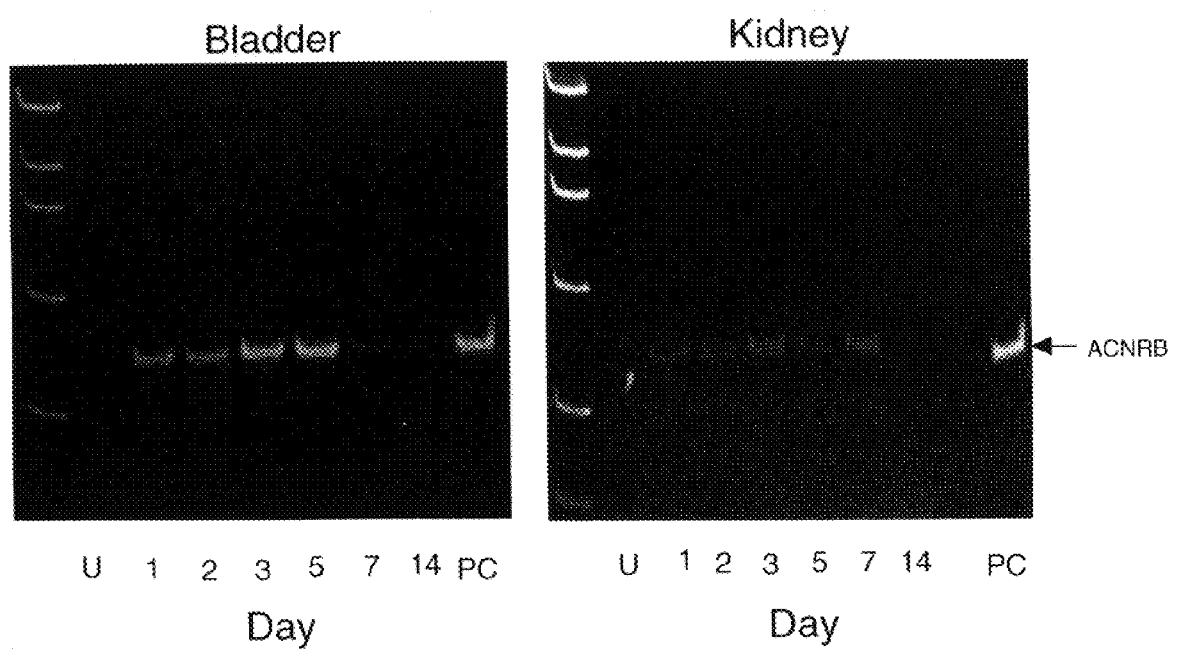
FIG. 6 depicts recombinant adenovirus transgene DNA in bladder and kidney homogenates after intravesical administration.

ACNRB DNA was detected in bladder tissue of all animals that received ACNRB, including those harvested 14 days after administration (FIG. 6, (left panel)). DNA was also recovered from the kidney homogenates, consistent with the ACNRB expression detected in this tissue (FIG. 6, right panel). No evidence for ACNRB DNA was detected in liver samples harvested during the study (data not shown). Samples from an untreated animal (U) and purified ACNRB DNA (PC) were used as negative and positive controls, respectively.

Because systemic administration of recombinant adenovirus results primarily in transgene expression in the liver (Li et al. *Human Gene Therapy* 4:403–409 (1993)), the absence of ACNRB DNA and expression in liver samples (FIGS. 5 and 6) suggests negligible systemic exposure of ACNRB after intravesical administration. Retrograde flow via the ureters may have contributed to the detection of ACNRB in the kidney.

The data presented above demonstrate transgene expression in the rodent bladder following intravesical administration of ACNRB. These studies further indicate that adenovirus-mediated gene transfer to the bladder epithelium can be enhanced by the presence of a delivery-enhancing agent, such as ethanol, in the formulation. One mechanism for the increased gene transfer may be the disruption of the protective glycosaminoglycan layer on the epithelial surface of the bladder. A single intravesical administration of ACNRB in a 20–30% (v/v) ethanol formulation results in transgene expression in the bladder that persists for approximately one week. Retrograde ureteral flow provides a likely explanation for the transient expression of ACNRB detected in the kidney. The absence of ACNRB expression and ACNRB DNA in the liver indicates limited systemic exposure after intravesical administration.

Example 5

Use of Detergent Formulations

To minimize side effects without losing gene transfer efficiency, other excipients were tested. Detergents are known to interact with cell membranes and form large pores without further damaging the cells. The efficiency of recombinant adenovirus formulated in less toxic detergents was studied in rats and mice gene transfer models.

rAd-βgal was formulated in different detergents at their critical micellization concentration to evaluate efficiency of gene transfer to the bladder epithelium. Female rats (about 200 g b/w, Harlan Sprague Dawley) were anesthetized with isoflurane and received a single intravesical administration of rAd-βgal ($1\times10^{11}$ PN/ml) in different detergent formulations (see Table I). Before instillation, bladders were flushed with PBS and then emptied. rAd-βgal was then instilled in a volume of 0.5 ml. The instilled solution was retained in the bladder for 45 minutes. The bladders were then flushed with PBS, and the animals were permitted to recover from the procedure. 48 hours after administration, the rats were sacrificed, the bladders harvested, and fixed in formalin. After fixation, the bladders were opened longitudinally so that the urothelium was exposed to the chromogen (Xgal), that is converted to a blue color, if reporter gene (β-galactosidase) expression is present. The luminal epithelial surface of the whole bladder was photographed an blue staining scored: + (minimal staining), ++ (moderate staining), +++ intense staining covering the whole bladder epithelial surface. The results are shown in Table I. Some of the anionic detergents (taurodeoxycholate), zwitterionic detergents (CHAPS, ZWITTERGENT®, and non-ionic detergents (Big CHAP, TRITON® X-100) enhanced gene transfer dramatically. Cationic detergents and some of the nonionic detergents (PLURONIC® F68, TWEEN®), did not have similar effects. In general, improvements of gene transfer were accompanied by cystitis. Zwiterionic detergents facilitated bladder stone formation.

Possible manifestations of cystitis as observed with ethanol were evaluated in mice using a 7 MM Big CHAP (2×CMC) or 0.05 mM TRITON®-X-100 detergent (CMC) formulation. The formulations were administered intravesically in a volume of 80 uL, and animals were observed over a 7-day interval. After sacrifice, bladders were paraffin-embedded, sectioned, and stained with hematoxylin and eosin for pathological evaluation. Only a slight macrophage infiltration into the bladder tissue was observed in mice treated with Big CHAP. Macrophages infiltrated more prominently (slight to mild) induced by TRITON®-X-100 detergent. In sharp contrast, significant cystitis was detected in animals treated with 22% ethanol.

| Excipient | Charge of Detergent | Dose (mM) | Gene Expression in Bladder Epithelium | Gross Pathology | Stability |
|---|---|---|---|---|---|
| Taurocholate | anionic | 6 | + | none | ND |
| Deoxycholate | anionic | 5 | + | Cystitis | ND |
| Taurodeoxycholate | anionic | 6 | +++ | Cystitis | + |
| Cetylpyridinium | cationic | 0.9 | + | none | − |
| Benzalkonium Chloride | cationic | 0.5% | <+ | none | − |
| Zwittergent ® 3–14 | zwitterionic | 4 | +++ | stone formation | ND |
| Chaps | zwitterionic | 7 | +++ | stone formation | + |
| Big Chap | non ionic | 3.5 | +++ | none | + |
| Deoxy Big Chap | non ionic | 1.5 | +++ | Cystitis | ND |
| Triton X-100 | non ionic | 0.05 | +++ | none | + |
| C12E8 | non ionic | 4 | ++ | none | ND |
| Octyl-β-D-Glucopyranoside | non ionic | 10 | ++ | none | ND |
| Pluronic F68 | non ionic | 0.04 | + | none | + |
| Tween 20 | non ionic | 2 | + | none | + |
| Tween 80 | non ionic | 0.02 | + | none | ND |
| Tween 80 | non ionic | 2 | + | none | + |

Example 6

Gene Transfer of ACNRB

Figure 9:
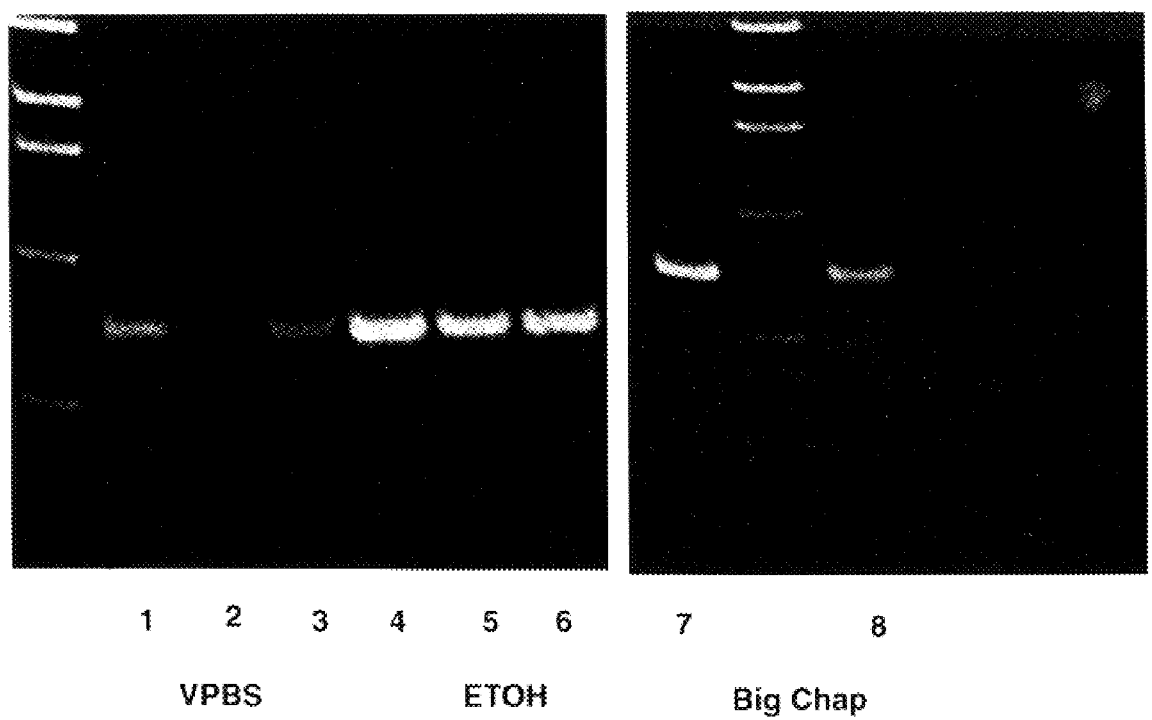
FIG. 9 depicts enhancement of recombinant adenovirus transgene expression in bladder tissue by using an ethanol (ETOH) or Big CHAP formulation.

In addition to the experiments with the reporter gene, a different set of studies was conducted to specifically evaluate gene transfer of ACNRB. Female ICR mice were anesthetized with avertine and each mouse received a single 80 μL intravesical administration of ACNRB. ACNRB (4×10$^{10}$ PN/mL) was formulated in VPBS, 22% (v/v) ethanol, or 3 mM Big CHAP. After the virus was retained in the bladder for 45 minutes, the animals were permitted to recover. Mice were sacrificed 48 hours after ACNRB administration, and bladders snap frozen in liquid nitrogen. Transgene expression was determined using RT-PCR. Tissues were rinsed in RNAse free water, homogenized, digested in Tri-Reagent (Molecular Research Center), and total cellular RNA extracted. ACNRB was probed using a 5' primer located in the CMV region of ACNRB vector, and a 3' primer resided in the 5' end of Rb genome. RT-PCR was performed in the Perkin Elmer 9600 GeneAmp PCR System. Cycling conditions were 10 min at 65° C., 8 min at 50° C., 5 min at 95° C. 32 cycles of PCR were performed, each cycle consisting of 30 sec at 94° C., 30 sec at 58° C., and 30 sec at 72° C. The 32nd cycle included a 10 min elongation step at 72° C. to ensure full extension of incomplete DNA fragments. ACNRB-RNA bands were stained with ethidium bromide. The results, enhanced expression using an ethanol or Big CHAP formulation, are shown in FIG. 9.

Example 7

Big CHAP Enhances Transgene Expression with Minimal Cystitis

Figure 7:
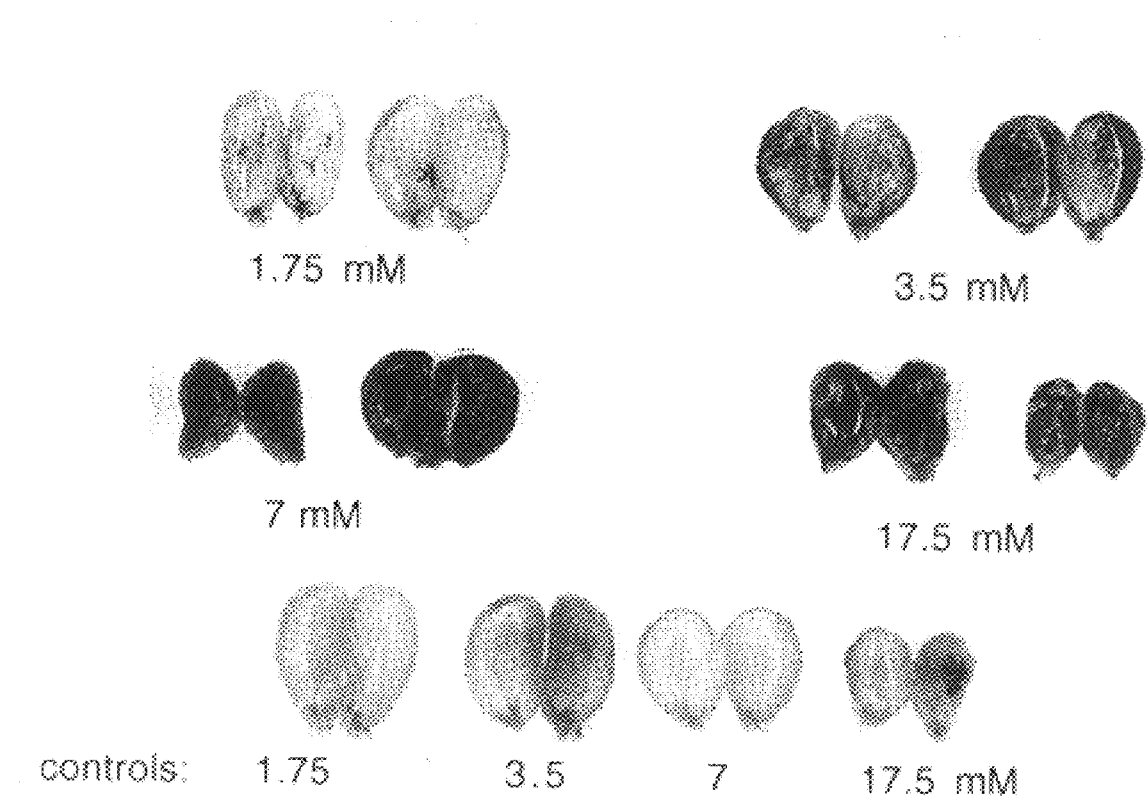
FIG. 7 depicts improvement of gene transfer to bladder epithelium using a Big CHAP (N,N,bis-(3-D-gluconamidopropyl)-cholamide (CALBIOCHEM® Biochemicals) formulation.

Because Big CHAP enhanced gene transfer with minimal cystitis, this formulation was selected for further evaluation, including concentration and dose-dependence in studies similar to those described above. Briefly, in anaesthetized female rats rAd-βgal (1×10$^{11}$ PN/ml) was administered into the bladder via an intravesical catheter. rAd-βgal was formulated in different concentrations of Big CHAP. A volume of 0.5 ml was injected and remained instilled in the bladder for 45 minutes. The animals were sacrificed 48 hours later, the bladder fixed in 4% formalin/glutaraldehyde, opened longitudinally, and the β-galactosidase enzyme activity measured using Xgal substrate. The intensity of blue staining correlates with the βgal-transgene expression. The figure shows the epithelial surface of Xgal stained bladders. The results indicate a concentration-dependent increase of gene transfer to the epithelium. The 3.5–7 mM concentrations of Big CHAP significantly improved gene transfer. The formulation alone (FIG. 7, lower panel) did not induce a blue color from the Xgal substrate. A higher concentration (17.5) mM did not notably improve gene transfer or expression, but induced cystitis in some of the animals tested.

Figure 8:
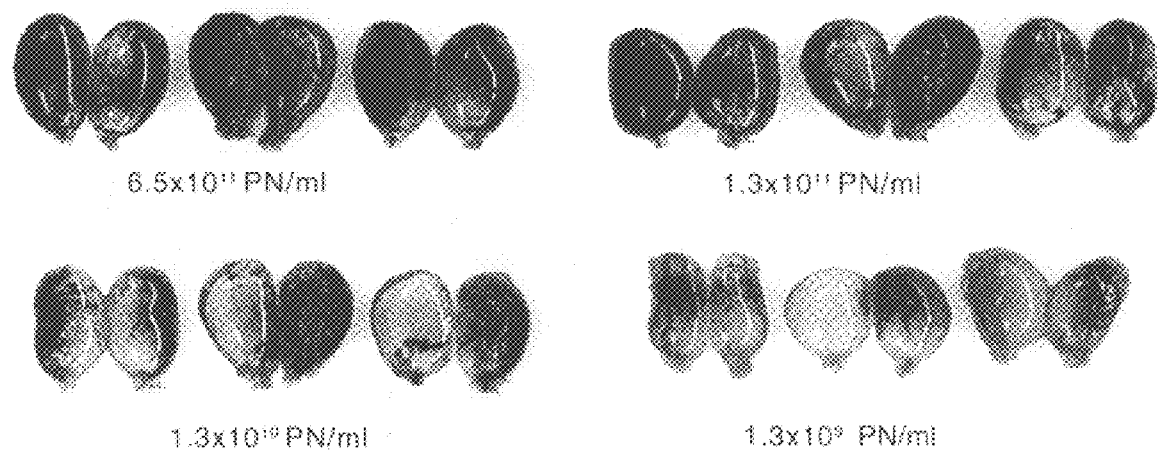
FIG. 8 depicts improvement of gene transfer to bladder epithelium using different concentrations of recombinant adenovirus in a 7 mM Big CHAP formulation.

Effects of higher recombinant adenovirus concentrations were also tested. Briefly, in anaesthetized female rats different concentrations of rAd-βgal, formulated in 7 mM Big CHAP were administered into the bladder via an intravesical catheter. The animals were sacrificed 48 hours later, the bladder fixed in 4% formalin/glutaraldehyde, opened longitudinally, and Xgal stained. FIG. 8 shows a concentration dependent increase of gene transfer to the epithelium. A concentration of 1.3×10$^{11}$ PN/ml induced maximal gene transfer. A higher concentration (6.5×10$^{11}$ PN/ml) did not notably improve the blue staining. In lower concentrations of rAd-βgal, 1.3×10$^{10}$ PN/ml, or 1.3×10$^9$ PN/ml, transgene expression reduced dose dependently. When 3.5 mM and 7 mM formulations were compared, β-galactosidase expression was similar, although the enhanced effect appeared more reproducible in animals treated with the 7 mM Big CHAP formulation.

Example 8

Transgene Expression in Tumors with Big CHAP Formulation

Figure 10:
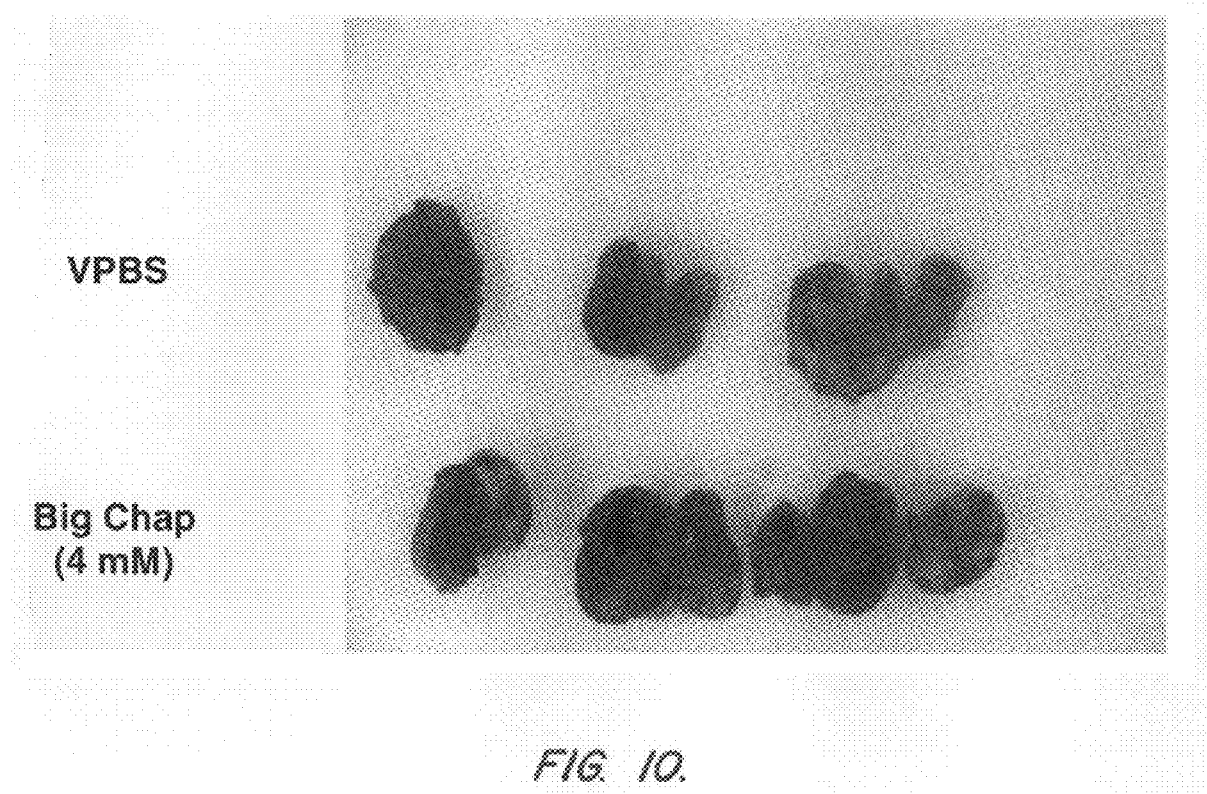
FIG. 10 depicts gene transfer to tumors using a 4 mM Big CHAP formulation.

Because initial investigations focused on animals with intact bladder epithelium, evaluated adenovirus mediated gene transfer in an animal model of transitional cell carcinoma was also studied. Tumors were induced in male Fisher rats by addition of 0.05% BBN in the drinking water for six months. rAd-βgal (1×10$^{11}$ PN/ml), formulated in 4 mM Big CHAP or VPBS was instilled into the bladder for 45 minutes by direct injection. β-gal expression was evaluated 48 hr after treatment. Consistent with earlier experiments using non-tumor bearing animals, gene transfer to tumor tissue was improved with the Big CHAP formulation compared to the VPBS formulation (FIG. 10).

Figure 12:
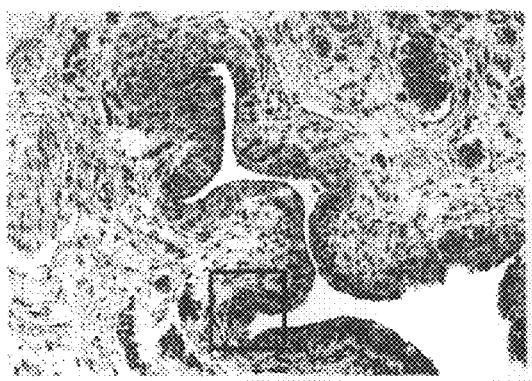
FIG. 12 depicts the expression of p53 in tumor tissue.
Figure 12:
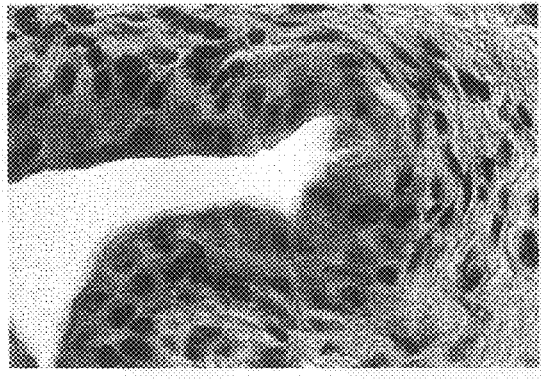

Gene transfer of rAd carrying the p53 gene (rAd-p53) (Wills et al. *Human Gene Therapy* 5:1079–1088 (1994)) was also tested in this animal model of bladder cancer. Briefly, bladder tumors were induced in female Fisher rats (Charles River) by addition of 0.05% BBN (N-butyl-N-N(4-hydroxybutyl)nitrosamine) in the drinking water for three months. rAD-p53 (1×10$^{11}$ PN/ml) was formulated in 7 mM Big CHAP. Under isoflurane anesthesia a catheter (24 G) was inserted into the bladder for administration. rAD-p53 was instilled into the bladder for 45 minutes. The animals were then allowed to recover from anesthesia. Twenty-four hr later, animals were sacrificed, and the bladder was fixed in formalin. After paraffin embedding and sectioning, p53 expression was assayed by immunohistochemistry using p53ES-kit (Oncogene) using AEC (AEC-kit, Vector Labs) as a substrate. Tissues were counterstained with hematoxylin. FIG. 12 shows p53 gene expression in the surface area of proliferative epithelium (left panel) and nuclear staining for p53 expression at higher magnification (right panel). No staining was detected in tumor tissue from untreated animals.

Example 9

Big CHAP Enhances Transgene Expression in Pig Urothelium

Figure 11:
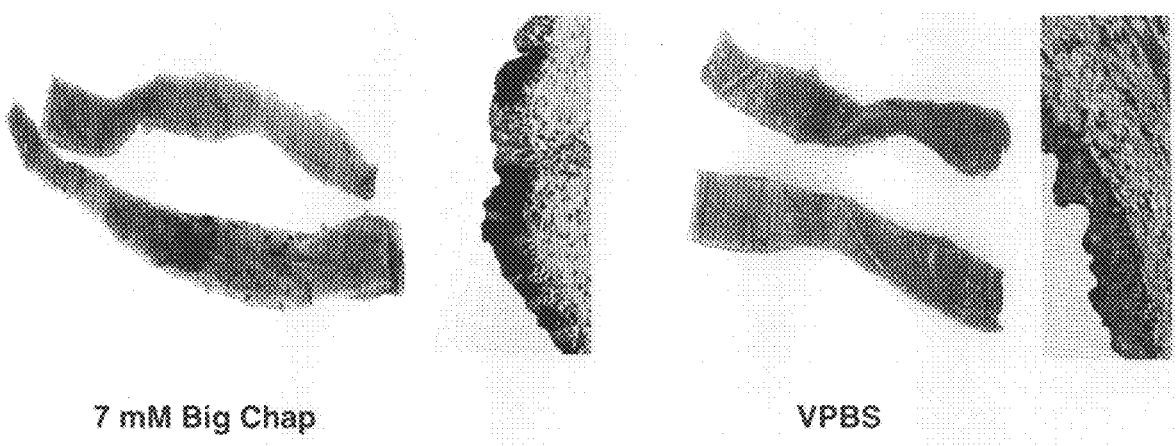
FIG. 11 depicts transgene transfer to pig bladder epithelium.

To simulate volumes expected for clinical investigation, the 7 mM Big CHAP formulation was tested in a chronically catheterized adult pig model in collaboration with SPRI Drug Safety and Metabolism. rAd-βgal (1×10$^{11}$ PN/ml) was formulated in VPBS or 7 mM Big CHAP. A volume of 50 ml was injected via the catheter into the bladder of the conscious animals. The instilled material was retained for 2 hr. The animals were sacrificed 48 hr later, and a central section of the bladder was harvested and stained for β-galactosidase expression. An increase in the intensity of gene expression was observed in the 7 mM Big CHAP treated pig compared to the VPBS treated pig (FIG. 11). Histologic evaluation demonstrated transduction of several epithelial layers using Big CHAP (left panel), but only superficial transduction with the VPBS buffer (right panel).

Example 10

Gene Transfer into Intestinal Epithelium in Rats

A slightly modification of the method of Sandberg et al. (*Human Gene Therapy* 5:323–329 (1994)) was used to prepare rat ileal segments for gene transfer studies. Briefly, female Sprague-Dawley rats were anesthetized with isoflurane. The abdominal cavity was opened and an ileal segment rostral from the last Peyer's patch isolated. The segment (about 3 cm) was cautiously cleared from food residues and both sides closed with atraumatic vascular clamps. rAd-βgal ($1 \times 10^{11}$ PN/ml), 0.5 ml volume, was directly injected into the segment with a 24 G needle and allowed to incubate for 45 minutes. rAd-βgal was formulated in 10 mM taurodeoxycholatic acid (in distilled water, sterile filtered) (Treatment group 1) or VPBS (Treatment Group 2). A third treatment group comprised animals treated with 10 mM taurodeoxycholatic acid. Thereafter, clamps were removed and a loose silk suture anchored on both ends for recognition at time of necropsy. The abdominal incision was closed and animals allowed to recover in their cages. Animals were sacrificed 48 hr later. The infected segment and a control segment were harvested in fixative for whole organ Xgal staining.

Figure 13:
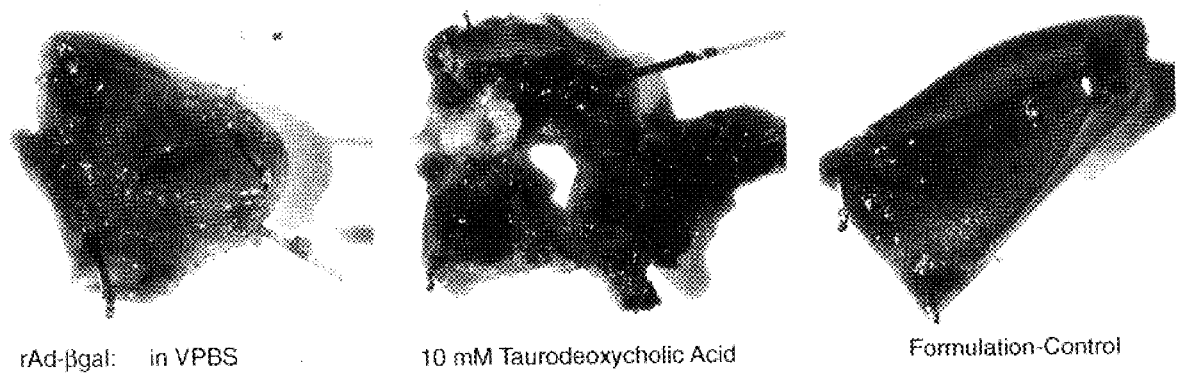
FIG. 13 depicts gene transfer to the muscosa of rat ileum.

The results are shown in FIG. 13. The extent of Xgal blue staining demonstrated evidence of transgene expression in the ileal sections. Enhanced gene transfer was evident in the detergent formulation (medial panel).

All publications and patent applications cited in this specification are herein incorporated by reference in their entirety as if each individual publication or patent application were specifically and individually indicated to be incorporated by reference.

As will be apparent to those skilled in the art to which the invention pertains, the present invention may be embodied in forms other than those specifically disclosed above, without departing from the spirit or essential characteristics of the invention. The particular embodiments of the invention described above, are, therefore to be considered as illustrative and not restrictive. The scope of the present invention is as set forth in the appended claims rather than being limited to the examples contained in the foregoing description.

What is claimed is:

1. A composition comprising a recombinant virus vector formulated in a buffer comprising a detergent.

2. The composition of claim 1, wherein the recombinant virus comprises a tumor suppressor gene.

3. The composition of claim 1, wherein the tumor suppressor gene is p53.

4. The composition of claim 1, wherein the tumor suppressor gene is a retinoblastoma gene.

5. The composition of claim 1, wherein the detergent is N,N,bis-(3-D-gluconamidopropyl)-cholamide (Big CHAP).

6. The composition of claim 1, wherein the detergent is octoylphenoxypolyethoxy-ethanol.

7. The composition of claim 1, wherein the concentration of the detergent is about 0.5–2× the critical micellization concentration.

8. The composition of claim 1, wherein the recombinant virus is an adenovirus.

9. A composition comprising a recombinant adenovirus, wherein the composition comprises about $10^9$–$10^{11}$ PN/ml recombinant adenovirus, about 2–10 mM Big CHAP or about 0.1–1.0 mM octylphenoxypolyethoxy-ethanol, phosphate buffered saline (PBS) (pH about 6.4–8.4), about 2–3% sucrose (w/v) and about 1–3 mM $MgCl_2$.

* * * * *